(12) United States Patent
Shah et al.

(10) Patent No.: US 12,178,698 B2
(45) Date of Patent: Dec. 31, 2024

(54) ARTIFICIAL SKIN

(71) Applicant: Nokia Technologies Oy, Espoo (FI)

(72) Inventors: Shreyas Shah, Dayton, NJ (US); Mingde Zheng, Bridgewater, NJ (US)

(73) Assignee: Nokia Technologies Oy, Espoo (FI)

( * ) Notice: Subject to any disclaimer, the term of this patent is extended or adjusted under 35 U.S.C. 154(b) by 729 days.

(21) Appl. No.: 17/252,554

(22) PCT Filed: Jul. 5, 2019

(86) PCT No.: PCT/FI2019/050526
§ 371 (c)(1),
(2) Date: Dec. 15, 2020

(87) PCT Pub. No.: WO2020/012064
PCT Pub. Date: Jan. 16, 2020

(65) Prior Publication Data
US 2021/0267749 A1    Sep. 2, 2021

(30) Foreign Application Priority Data

Jul. 13, 2018 (EP) .................................... 18183393

(51) Int. Cl.
*A61F 2/10* (2006.01)
*A61B 5/00* (2006.01)
(Continued)

(52) U.S. Cl.
CPC ............ *A61F 2/105* (2013.01); *A61B 5/0066* (2013.01); *A61B 5/01* (2013.01); *A61B 5/14532* (2013.01);
(Continued)

(58) Field of Classification Search
CPC .............. A61F 2/105; A61F 2250/0001; A61F 2250/0002; A61B 5/0066; A61B 5/01;
(Continued)

(56) References Cited

U.S. PATENT DOCUMENTS 5,195,145 A * 3/1993 Backus .............. G06V 40/1335
382/126
6,165,389 A    12/2000 Asher et al.
(Continued)

FOREIGN PATENT DOCUMENTS

CA        2583034 A1    9/2007
CN    107412872 A    12/2017
(Continued)

OTHER PUBLICATIONS

Partial European Search Report received for corresponding European Patent Application No. 17192589.4, dated Feb. 22, 2018, 14 pages.
(Continued)

*Primary Examiner* — Paul B Prebilic
(74) *Attorney, Agent, or Firm* — Harrington & Smith

(57) ABSTRACT

The application relates to an apparatus which comprises at least one portion of artificial skin (103) and a plurality of sensors (105) dispersed within the at least one portion of artificial skin (103). The plurality of sensors (105) have at least one physical property which is configured to be modified when the plurality of sensors (105) are exposed to a parameter such that the modification of the physical property can be detected by an external detector (211). The application also relates to detection systems comprising such apparatus.

14 Claims, 4 Drawing Sheets

(51) Int. Cl.
    *A61B 5/01*     (2006.01)
    *A61B 5/145*    (2006.01)
(52) U.S. Cl.
    CPC ...... *A61B 5/14539* (2013.01); *A61B 5/14542*
                (2013.01); *A61B 5/4875* (2013.01)
(58) Field of Classification Search
    CPC ............ A61B 5/14532; A61B 5/14539; A61B
                5/14542; A61B 5/4875; A61B 2505/00;
                A61B 2505/05; A61B 2505/07; A61B
                2505/09; A61B 2560/0462; A61B
                2562/0271; A61B 2562/0276; A61B
                2562/028; A61B 2562/046; A61B
                2562/14; A61B 2562/164
    See application file for complete search history.

(56)            References Cited

U.S. PATENT DOCUMENTS

| | | | |
|---|---|---|---|
| 9,042,967 B2 | 5/2015 | Dacosta et al. | |
| 2004/0116866 A1* | 6/2004 | Gorman | A61M 37/00 604/93.01 |
| 2007/0188749 A1 | 8/2007 | Brady et al. | |
| 2008/0076994 A1* | 3/2008 | Hoarau | A61B 5/14552 600/323 |
| 2008/0281244 A1* | 11/2008 | Jacobs | A61B 5/4839 602/41 |
| 2012/0237605 A1 | 9/2012 | Messersmith et al. | |
| 2013/0244120 A1* | 9/2013 | Yu | H01M 10/0567 429/339 |
| 2013/0261409 A1 | 10/2013 | Pathak et al. | |
| 2014/0011705 A1* | 1/2014 | Liu | G01N 33/587 435/23 |
| 2014/0106468 A1* | 4/2014 | Boersma | G01N 21/7743 422/69 |
| 2014/0298928 A1* | 10/2014 | Duesterhoft | A61M 1/73 73/865.8 |
| 2016/0153975 A1 | 6/2016 | Biris et al. | |
| 2017/0255030 A1* | 9/2017 | Etzkorn | G02C 7/049 |
| 2017/0360986 A1 | 12/2017 | Paten et al. | |
| 2018/0055359 A1 | 3/2018 | Shamim et al. | |
| 2018/0143091 A1 | 5/2018 | Wood et al. | |

FOREIGN PATENT DOCUMENTS

| | | |
|---|---|---|
| EP | 2500314 A1 | 9/2012 |
| EP | 3449882 A1 | 3/2019 |
| EP | 3460472 A1 | 3/2019 |
| JP | 2009269998 A | 11/2009 |
| KR | 10-1596195 B1 | 2/2016 |
| WO | 01/55704 A1 | 8/2001 |
| WO | 02/01228 A2 | 1/2002 |
| WO | 2004/042403 A2 | 5/2004 |
| WO | 2008/018933 A2 | 2/2008 |
| WO | 2011/119822 A1 | 9/2011 |
| WO | 2017/049284 A1 | 3/2017 |
| WO | 2017/122178 A1 | 7/2017 |
| WO | 2017/195038 A1 | 11/2017 |

OTHER PUBLICATIONS

Extended European Search Report received for corresponding European Patent Application No. 17192589.4, dated Jun. 8, 2018, 15 pages.

Invitation to Pay Additional Fees and Partial Search Report received for corresponding Patent Cooperation Treaty Application No. PCT/FI2018/050669, dated Oct. 25, 2018, 15 pages.
International Search Report and Written Opinion received for corresponding Patent Cooperation Treaty Application No. PCT/FI2018/050669, dated Dec. 17, 2018, 20 pages.
Office action received for corresponding European Patent Application No. 17192589.4, dated Jul. 16, 2020, 6 pages.
Ochoa et al., "Flexible Sensors for Chronic Wound Management", IEEE Reviews in Biomedical Engineering, vol. 7, 2014, pp. 73-86.
"Outpatient (Clinic/Private Office)", Integra Limit Uncertainty, Retrieved on Dec. 15, 2020 2008, Webpage available at : http://www.dermasciences.com/algicell-ag.
You et al., "Silver Nanoparticle Loaded Collagen/Chitosan Scaffolds Promote wound Healing via Regulating Fibroblast Migration and Macrophage Activation", Scientific Reports, vol. 7, 2017, pp. 1-11.
McLister et al., "New Developments in Smart Bandage Technologies for Wound Diagnostics", Advanced materials, Jan. 2016, pp. 1-6.
Mehmood et al., "A Flexible and Low Power Telemetric Sensing and Monitoring System for Chronic Wound Diagnostics", Biomedical engineering online, vol. 14, No. 17, 2015, pp. 1-17.
Mostafalu et al., "Wireless Flexible Smart Bandage for Continuous Monitoring of Wound Oxygenation", IEEE Transactions on Biomedical Circuits and Systems, vol. 9, No. 5, Oct. 2015, pp. 670-677.
Rahimi et al., "A Wireless Strain Sensor for Wound Monitoring with Direct Laser-defined Patterning on a Commercial Dressing", IEEE 29th International Conference on Micro Electro Mechanical Systems (MEMS), Jan. 24-28, 2016, pp. 481-484.
Tamayol et al., "Flexible pH-Sensing Hydrogel Fibers for Epidermal Applications", Advanced healthcare materials, vol. 5, Mar. 2016, pp. 711-719.
Guinovart et al., "Bandage-Based Wearable Potentiometric Sensor for Monitoring Wound pH", Electroanalysis, vol. 26, 2014, pp. 1-9.
Shevchenko et al., "A Review of Tissue-engineered Skin Bioconstructs Available for Skin Reconstruction", Journal of the Royal Society Interface, vol. 7, 2010, pp. 229-258.
Halim et al., "Biologic and Synthetic Skin Substitutes: An overview", Indian Journal of Plastic Surgery, vol. 43, 2010, pp. S23-S28.
Ng et al., "Proof-of-concept: 3D Bioprinting of Pigmented Human Skin Constructs", Biofabrication, vol. 10, 2018, pp. 1-13.
Kuck et al., "Evaluation of Optical Coherence Tomography as a Non-invasive Diagnostic Tool in Cutaneous Wound Healing", Skin research and technology, vol. 20, 2014, pp. 1-7.
Bruinink, "Biosensor-Bearing Wound Dressings for Continuous Monitoring of Hard-to-Heal Wounds: Now and Next", Biosensors and Bioelectronics Open Access, vol. 2018, No. 1, 2018, pp. 1-19.
Khan et al., "Real-time wound Management through Integrated pH Sensors: A Review", Sensor Review, vol. 35, No. 2, 2015, pp. 183-189.
Extended European Search Report received for corresponding European Patent Application No. 18183393.0, dated Feb. 14, 2019, 8 pages.
Xu et al., "Multifunctional Wearable Sensing Devices Based on Functionalized Graphene Films for Simultaneous Monitoring of Physiological Signals and Volatile Organic Compound Biomarkers", ACS Appl. Mater. Interfaces, vol. 10, No. 14, 2018, pp. 11785-11793.
International Search Report and Written Opinion received for corresponding Patent Cooperation Treaty Application No. PCT/FI2019/050526, dated Oct. 7, 2019, 17 pages.

\* cited by examiner

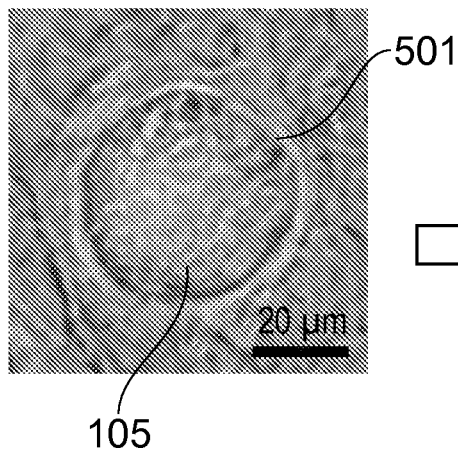 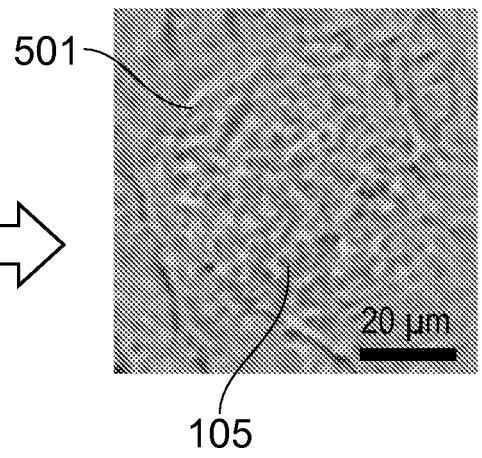
FIG. 5A FIG. 5B
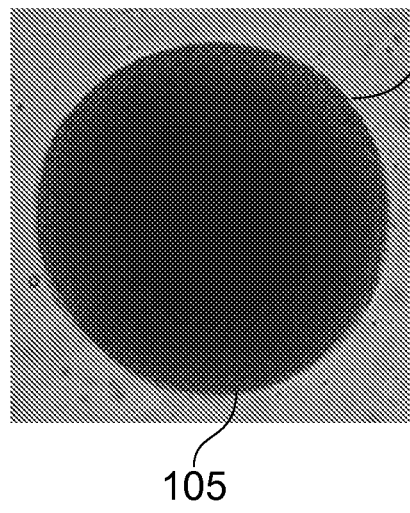 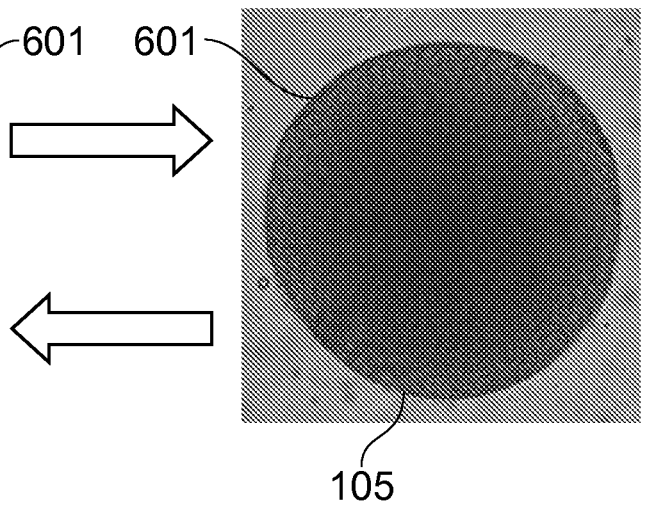
FIG. 6A FIG. 6B

ARTIFICIAL SKIN

RELATED APPLICATION

This application claims priority to PCT Application No. PCT/FI2019/050526, filed on Jul. 5, 2019, which claims priority to European Application No. 18183393.0, filed on Jul. 13, 2018, each of which is incorporated herein by reference in its entirety.

TECHNOLOGICAL FIELD

Examples of the present disclosure relate to artificial skin. Some relate to artificial skin that can be used to sense biological parameters of a subject.

BACKGROUND

Artificial skin can be used to cover wounds or other damage to a subject's skin. When the artificial skin is applied to a subject's skin it is difficult to determine the conditions underneath the surface of the applied artificial skin. This can make it difficult to determine how a wound is healing.

BRIEF SUMMARY

According to some, but not necessarily all, examples of the disclosure there may be provided an apparatus comprising: at least one portion of artificial skin; a plurality of sensors dispersed within the at least one portion of artificial skin; wherein the plurality of sensors have at least one physical property which is configured to be modified when the plurality of sensors are exposed to a parameter such that the modification of the physical property can be detected by an external detector.

The apparatus may comprise a protective surface provided overlaying the at least one portion of artificial skin. The protective surface provides an interface between the plurality of sensors and the external detector.

The at least one portion of artificial skin may be configured to integrate with the skin of a subject.

The at least one portion of artificial skin may be configured to cover a wound of a subject.

The at least one portion of artificial skin may be configured to conform to the shape of a subject's damaged skin.

The at least one portion of artificial skin may comprise a matrix of skin tissue which is configured to support the plurality of sensors.

The plurality of sensors may comprise functionalized particles.

At least one of the functionalized particles may be configured to bind to a chemical entity so that the binding modifies a physical property of the functionalized particle.

The functionalized particles may have a diameter which is less than 100 micrometers.

The apparatus may comprise a plurality of different types of sensors where the different types of sensors are configured to detect different parameters. The apparatus may comprise a plurality of different types of sensors where the different types of sensors have different shapes.

The parameter that is detected by the plurality of sensors may comprise at least one of, glucose levels, bacteria, temperature, pH level, chemical entity, moisture, oxygenation levels.

The physical property of the plurality of sensors that is modified may comprise at least one of, an optical property, a size of the sensor.

The external detector may comprise an optical coherence tomography detector.

According to some, but not necessarily all, examples of the disclosure there may be provided a detection system comprising an apparatus as claimed in any preceding claim and a detector configured to detect modification of the physical properties of the sensors.

BRIEF DESCRIPTION

Some example embodiments will now be described with reference to the accompanying drawings in which:

FIGS. 5A and 5B show an example sensor; and

FIGS. 6A and 6B show an example sensor.

DETAILED DESCRIPTION

Figure 1:
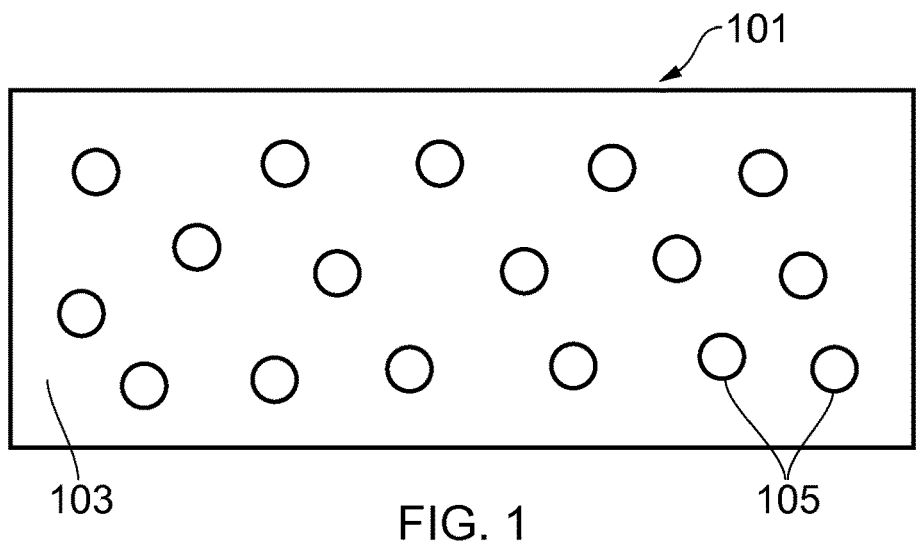
FIG. 1 shows an example apparatus.

The Figures illustrate an apparatus 101 comprising at least one portion of artificial skin 103 and a plurality of sensors 105 dispersed within the at least one portion of artificial skin 103. The plurality of sensors 105 have at least one physical property which is configured to be modified when the plurality of sensors 105 are exposed to a parameter. The physical property could be an optical property of the sensors 105. For example it could be the way in which the sensor 105 interacts with light. In other examples the physical property could be the size and/or shape of the sensor 105.

The modification of the physical property which is caused by the exposure to the parameter can be detected by an external detector. The external detector could be a separate device to the apparatus 101. For example the external detector could be a scanning device which can be moved around different parts of the subject's body so as to enable the properties of different sensors 105 to be detected.

This provides the technical effect of enabling the parameters to be detected and monitored using a portion of artificial skin 105. This detection of the parameters enables the conditions within the skin to be monitored internally.

The apparatus 101 may be for use as a skin graft.

FIG. 1 shows an example apparatus 101 according to examples of the disclosure. The apparatus 101 comprises a portion of artificial skin 103 and a plurality of sensors 105 dispersed within the artificial skin 103. It is to be appreciated that the apparatus 101 could comprise additional components that are not shown in FIG. 1. For instance in some examples the apparatus 101 could comprise a protective surface overlaying the artificial skin 103 or any other suitable additional components.

The artificial skin 103 comprises any suitable material which may be used as a replacement portion of skin for a subject. The artificial skin 103 may be configured to cover a wound or other region of damaged skin of a subject. In some examples the artificial skin 103 could be configured to be inserted into a subject's skin, for example, as part of a biopsy or other process. In some examples the artificial skin 103 could be configured to be inserted into a subject's skin so as to replace some healthy skin with artificial skin 103.

The artificial skin 103 may comprise a flexible material. The artificial skin 103 may be flexible so that when the apparatus 101 is attached to a subject the artificial skin 103 conforms to the existing skin of the subject. The artificial skin 103 may be flexible so that it allows the artificial skin to bend and/or stretch as needed when it forms part of the skin of the subject.

The artificial skin 103 may comprise a soft material. The artificial skin 103 may be soft so that it deforms when mechanical forces are applied to the artificial skin 103 by the subject. For example, the artificial skin 103 may be soft enough so that it is deformed when mechanical stress is applied by the subject bending or flexing the artificial skin 103 by moving. This deformation may help to protect any damaged skin and may prevent the mechanical stress from being imparted to any damaged skin underneath, or contact with, the artificial skin 103.

In the example of FIG. 1 the portion of artificial skin 103 that is shown comprises a substantially rectangular shape. It is to be appreciated that the artificial skin 103 could have any suitable shape in examples of the disclosure. For example, the portion of artificial skin 103 could be formed to have a shape corresponding to the damaged area of skin for which the apparatus 101 is to be used to cover. In such examples the artificial skin 103 could be printed, using a three dimensional printer or other suitable means, to have a shape corresponding to the damaged area of skin. The shape corresponding to the damaged area of skin could be a shape which fills or substantially fills any missing sections of the damaged skin. The shape corresponding to the damaged area of skin could be a shape which covers all of, or substantially all of, the damaged area of skin.

The portion of artificial skin 103 may be configured to integrate with the the skin of the subject. When the apparatus is in use the artificial skin 103 may be applied to a subjects' skin so that the artificial skin is in direct contact with the subject's existing skin. The portion of artificial skin 103 may be configured to remain on the subject's skin and integrate with the the subject's skin to form part of the subject's skin. In some examples the portion of artificial skin 103 may be integrated with the the subject's skin at a cellular level. For example, where the apparatus 101 is used to replace lost or damaged skin the artificial skin 103 may be left to form part of the subject's skin even after the damaged skin has healed. The artificial skin 103 does not need to be removed from the subject's skin.

The artificial skin 103 may be configured to provide a protective layer to replace a portion of the subject's skin. The protective layer may be impermeable, or at least partially impermeable to, bacteria and other factors that may affect the healing of a wound. The protective layer may prevent factors such as bacteria from coming into contact with the subject's body underneath the artificial skin 103. In some examples the artificial skin 103 may be configured to enable moisture balance within the area of the damaged skin so as to facilitate recovery of the damaged skin. In some examples the artificial skin 103 may be configured to enable moisture balance within the area of the damaged skin so as to optimise, or substantially optimise recovery of the damaged skin.

The artificial skin 103 may comprise a synthetic material and/or a biological material. The synthetic material could comprise a polymeric material. The synthetic material could comprise, polystyrene, polyacrylamide, polymethylmethacrylate, polyethylene glycol, poly(lactic acid), poly(glycolic acid), poly(lactide-co-glycolic acid), poly(N-isopropylacrylamide), poly($\varepsilon$-caprolactone), poly(3-hydroxybutyrate-co-3-hydroxyvalerate) or any other suitable material or combination of materials.

The biological material could comprise any material that occurs naturally in some living organisms. In some examples the biological material could comprise chitosan, collagen, alginate, dextran, gelatin, fibrin, albumin, glycosaminoglycans, fibronectin, laminin, hyaluronan, biological cells such as fibroblasts and stem cells, or any other suitable material or combination of materials.

The material that is used to form the artificial skin 103 may comprise a matrix of skin tissue that can be used to support the plurality of sensors 105. The matrix may be formed from polymeric films, hydrogels, or fibrous strands of the material used for the artificial skin 103.

The plurality of sensors 105 are dispersed throughout the artificial skin 103. The plurality of sensors 105 may be supported by the matrix which is formed by the artificial skin 103. In some examples the plurality of sensors 105 may be homogenously distributed throughout the artificial skin 103. In some examples at least some of the sensors 105 are entirely embedded within the artificial skin 103. When a sensor 105 is entirely embedded within the artificial skin 103 it is completely surrounded by the material of the artificial skin 103 so that no part of the sensor 105 is exposed. When a sensor 105 is entirely embedded within the artificial skin 103 the sensor 105 does not form part of an outer surface of the apparatus 101. This may ensure that the sensors 105 detect parameters within the subject's skin rather than external parameters.

The plurality of sensors 105 may comprise any means which may have a physical property which is modified when a sensor 105 is exposed to a parameter so that the modification in the physical property can be detected by a remote detector. The physical property that is modified could comprise an optical property. The optical property could be a property which defines the way that the sensor 105 interacts with light or other electromagnetic radiation. For example the optical property could be the refractive index, a spectral response of the sensor 105 or any other suitable property.

The optical property of the sensors 105 could be a property that can be detected by probing the apparatus 101 with light of an appropriate wavelength. For example, changes in the refractive index of the sensors 105 could be determined by directing light into the apparatus 101. In some examples spectral or spectroscopic changes of the sensors 105 could be determined by directing light into the apparatus 101. The light that is used to probe the apparatus 101 could be visible light, infrared light or any other suitable wavelength of light.

In some examples the physical property of the sensors 105 that is detected could be a size and/or shape of the sensors 105. The size and/or shape of the sensors 105 could be detected by probing the apparatus 101 with light of the appropriate wavelength. This may enable an image of the sensors 105 to be obtained which can be used to detect changes in the size and/or shape of the sensors 105.

In some examples the sensors 105 could comprise functionalized particles. The sensors 105 could be functionalised so that a physical property of the particles is modified in response to a parameter. The functionalising of the particles could comprise the addition of a chemical entity such that the chemical entity causes a change in the physical property when a parameter is detected.

The functionalized particles may be any suitable size. The functionalized particles may have a size which enables them to be distributed throughout a portion of artificial skin 103. The functionalized particles may have a size so that they can be viewed in images obtained using optical coherence tomography or other suitable imaging techniques. In some examples the functionalized particles may have a diameter of less than 100 micrometres. In some examples the functionalised particles may have a diameter greater than 500 nanometres.

In the example shown in FIG. 1 the plurality of sensors 105 are all the same type or similar type. That is, each of the plurality of sensors 105 is a similar size and shape and each of the plurality of sensors 105 is configured to detect the same parameter or parameters. It is to be appreciated that in other examples of the disclosure the apparatus 101 may comprise a plurality of different types of sensors 105. The different types of sensors 105 could have different sizes or shapes. In some examples the different types of sensors 105 could be configured to detect different parameters. In some examples the different types of sensors 105 could be configured to have different levels of sensitivity to the same parameter.

The sensors 105 may be configured to detect any suitable parameter. The parameter that is detected by the sensors 105 could be an internal parameter. The internal parameter could be a parameter that is found within the subject's skin. The parameter that is detected by the plurality of sensors comprises at least one of, glucose levels, bacteria, temperature, PH level, chemical molecule, moisture, oxygenation levels or any other suitable parameter. The chemical entity could comprise proteins, drug metabolites or any other suitable parameter. The parameter could provide an indication of how the wound, or other damaged skin, is healing. In some examples the parameter could provide an indication of longer term condition of a subject. For example the measurement of the blood glucose levels could provide an indication of a subject's health independently of a wound healing process.

The sensors 105 could comprise any suitable materials. For example the sensors 105 could comprise inorganic materials such as gold, silver, silica, titania, silicone, ceramic, glass, iron oxide or any other suitable material. In some examples the sensors 105 could comprise a biological material such as chitosan, collagen, alginate, dextran, gelatin, fibrin, albumin, glycosaminoglycans, fibronectin, laminin, hyaluronan, biological cells such as fibroblasts and stem cells, or any other suitable material or combination of materials. In some examples the sensors 105 coulde comprise a synthetic material polystyrene, polyacrylamide, polymethylmethacrylate, polyethylene glycol, poly(lactic acid), poly(glycolic acid), poly(lactide-co-glycolic acid), poly(N-isopropylacrylamide), poly(ε-caprolactone), poly(3-hydroxybutyrate-co-3-hydroxyvalerate) or any other suitable material or combination of materials. The material used for the sensors 105 could be functionalized to increase the affinity of the sensor 105 to a parameter.

The external detector could comprise any means which may be configured to detect the modification of the physical property of the sensors 105. In some examples the external detector could comprise an optical detector such as an optical coherence tomography detector or other suitable detector. The optical detector could comprise any means which may be configured to probe the apparatus 101 with an optical signal and detect an output which is dependent upon the physical property. The optical detector could use visible light, infrared light or any other suitable wavelength of light.

The external detector could be remote from the apparatus 101 so that the external detector is not physically coupled to the apparatus 101 or the user. For example the external detector could comprise a mobile scanner that can be moved to scan an apparatus 101 on any suitable part of a subject. In other examples the detector could be provided in a hospital or other suitable location and the subject could be positioned close to the detector to enable the apparatus 101 to be probed.

FIGS. 2A to 2D show components of an example apparatus 101 according to examples of the disclosure.

Figure 2A:
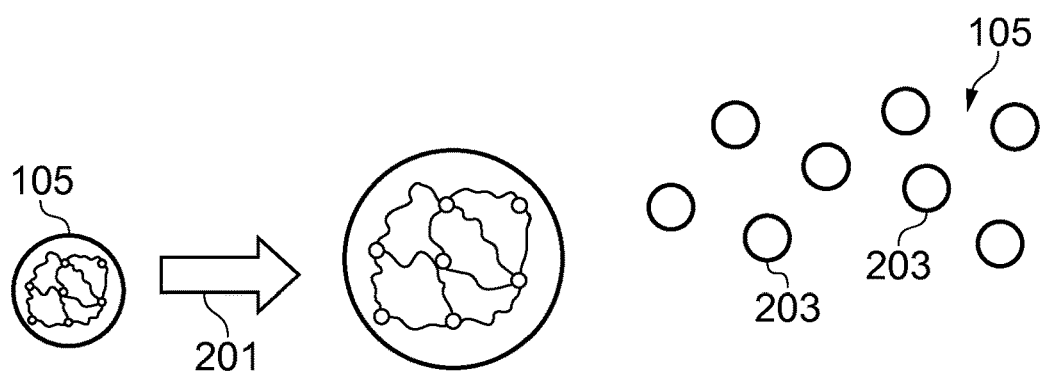
FIGS. 2A to 2D show components of an example apparatus.

FIG. 2A shows example sensors 105 that may be used. In the example of FIG. 2A the sensors 105 comprise functionalized particles 203. In the example of FIG. 2A the functionalized particles 203 comprise spherical particles. It is to be appreciated that other shapes of particles could be used in other examples. For instance the particles could comprise fibres, elongated shapes or any suitable shapes.

The functionalized particles 203 may be fabricated so that the functionalized particles 203 have a selected size and/or shape. The size and/or shape of the functionalized particles 203 may be selected so as to facilitate the detection of a specific parameter. The size and/or shape of the functionalized particles 203 may be selected so as to improve the efficiency with which the functionalized particles 203 can detect the specific parameter. The functionalized particles 203 may be fabricated using any suitable processes such as bottom-up chemical synthesis, homogenization, microfluidics and/or any other suitable process.

The functionalized particles 203 may be functionalized so as to increase the affinity of the functionalized particles 203 to a particular chemical entity or structure. This may make it easier for the functionalized particles 203 to bind to another chemical entity. In some examples the functionalized particles 203 may be functionalized so that the functionalized particles 203 bind selectively to a particular chemical entity. This ensures that any change in the physical properties of the sensors 105 can be attributed to the presence of the selected chemical entity. As an example, the sensors 105 may be intended to detect glucose levels. In such examples the functionalized particles 203 may be configured to comprise phenylboronic acids derivatives which can be reversibly bound to glucose. In some examples the functionalized particles 203 may be configured to comprise aptamers which can be reversible bound to target nucleic acids, proteins, peptides or any other suitable parameters.

The functionalized particles 203 could comprise microparticles, nanoparticles or any other suitable sized particles.

In the example of FIG. 2A the functionalized particles 203 are configured to increase in size in the presence of a parameter as indicated by the arrow 201. This increase in size acts as an amplifier of the parameter and may enable the presence of the parameter to be quantified.

In some examples the increase in size of the functionalized particles 203 could be caused by the functionalized particles 203 binding to a parameter. For example a chemical entity of the functionalized particles 203 could bind to a parameter comprising a corresponding chemical entity which increases the size of the functionalized particles 203. In some examples the binding could also change the shape of the functionalized particles 203.

In some examples the parameter could provide an indication of the progress of a wound healing process. For example the parameter could comprise bacteria, temperature, pH level, chemical entity, moisture, oxygenation levels or any other parameter that changes as a wound heals. In some examples the parameter could be an indication of a subject's general health. For example glucose levels or temperature may provide an indication of a subject's physical condition independently of a wound healing process.

Figure 2B:
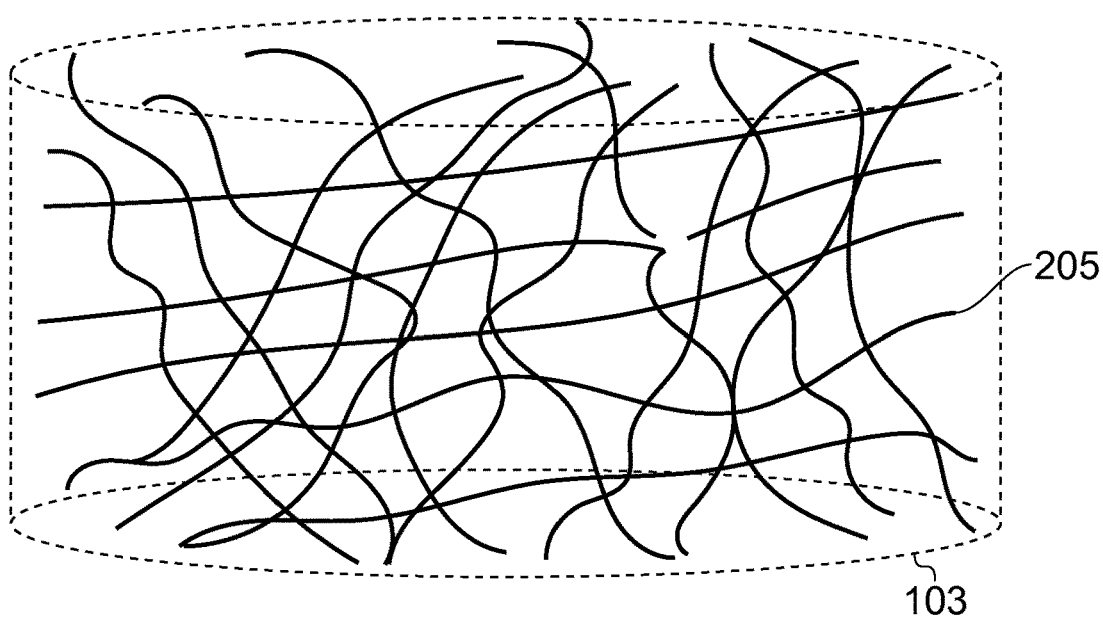

FIG. 2B shows some example artificial skin 103 before the plurality of sensors 105 are added. The artificial skin 103 comprises a matrix 205 of skin tissue that can be used to support the plurality of sensors 105. The matrix 205 may be formed from fibrous strands of the material used for the artificial skin 103.

The artificial skin 103 may be a flexible material that can be configured to conform with a subject's skin. In some examples the artificial skin 103 could be provided as a gel which can be coated onto a subject's skin. In some examples the artificial skin 103 could be formed by a process such as three dimensional printing so as to fit into a specific portion of a subject's skin.

Figure 2C:
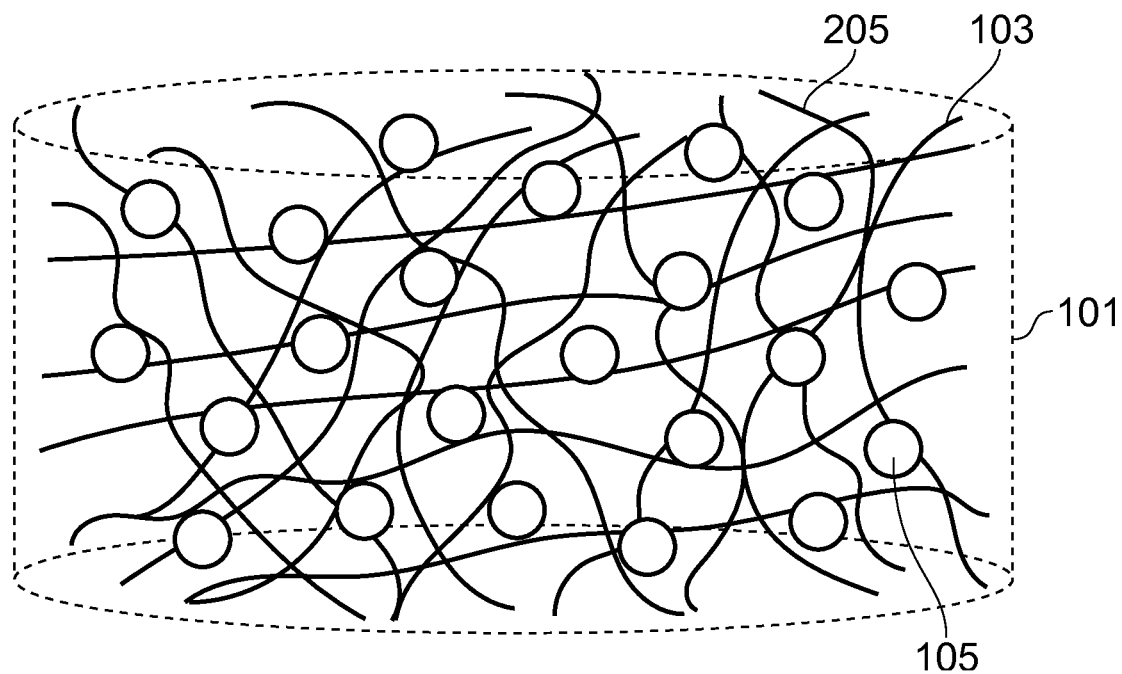

FIG. 2C shows an example apparatus 101 which has been formed from plurality of sensors 105 as shown in FIG. 2A and the artificial skin 103 as shown in FIG. 2B. The apparatus 101 may be formed by combining the sensors 105 with the artificial skin 103. Any suitable method may be used to combine the sensors 105 with the artificial skin 103. For instance, where the artificial skin 103 is formed from a gel or liquid the plurality of sensors 105 could be mixed into the artificial skin 103.

The plurality of sensors 105 may be combined with the artificial skin 103 so that there is a selected density of sensors 105 within the skin 103. The density of sensors 105 may be selected so as to enable a parameter to be adequately detected. In some examples the density of sensors 105 may be selected so as to enable a detected parameter to be quantified.

In some examples the plurality of sensors 105 may be homogenously distributed throughout the artificial skin 103. The homogenous distribution of the plurality of sensors 105 may enable the detected parameter to be quantified. In some examples the homogenous distribution of the plurality of sensors 105 may enable more detailed information about the healing of a wound, or other biometric parameters, to be obtained.

Figure 2D:
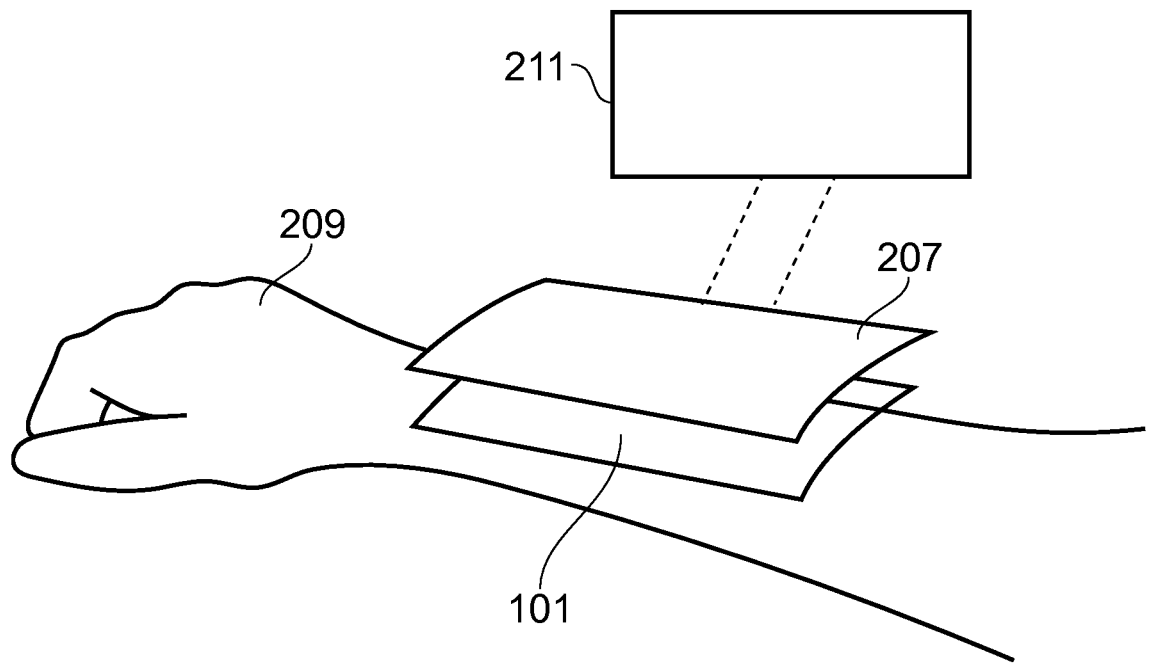

FIG. 2D shows an example apparatus 101 in use. In this example the apparatus 101 also comprises a protective surface 207 which is provided overlaying the portion of artificial skin 103. The protective surface 207 may provide an outer surface of the apparatus 101. The protective surface 207 could comprise a partially permeable membrane which enables some particles to pass through the protective surface 207 but prevents some other particles from passing through. For example, the protective surface 207 could enable some gases to pass through but may be configured to prevent moisture loss through the membrane.

In the example of FIG. 2D the protective surface 207 provides an interface between the plurality of sensors 105 within the apparatus 101 and an external detector 211. The protective surface 207 may be transparent to any light, or other probing means, that is used by the detector 211. In some examples the protective surface 207 may be partially transparent.

The protective surface 207 may also be configured to provide mechanical support to the artificial skin 103. The protective surface 207 may be flexible so as to enable the apparatus 101 which comprises the protective surface to conform to the skin of the subject.

The protective surface 207 may comprise any suitable material. In some examples the protective surface 207 may comprise a silicone based film or any other suitable material.

In the example of FIG. 2D the apparatus 101 has been applied to the skin on a subject's arm 209. Any suitable means may be used to apply the apparatus 101 to the subject's arm 209. In some examples the artificial skin 103 could be formed as a gel with the sensors 105 suspended within the gel. The gel may then be coated onto a portion of the subject's skin. For example the gel may be coated over a wound or other portion of damaged skin. In some examples the portion of artificial skin 103 may be sized and shaped so as to fit into a specific portion of skin of the subject. For example, three dimensional printing, or any other suitable method, may be used to form a portion of artificial skin 103 which is sized and shaped so as to fit into a specific wound.

In the example of FIG. 2D a detector 211 is used to monitor the physical properties of the plurality of sensors 105. In the example of FIG. 2D the detector 211 comprises a hand-held scanner that can be scanned across the apparatus 101 and/or other parts of the subject's body. In other examples the detector could be a fixed detector which could be located in an environment such as a hospital or a laboratory. The subject could then be positioned in proximity to the detector 211 to enable the physical properties of the sensors 105 to be monitored.

In some examples the detector 211 could be an optical detector. This may enable optical properties of the sensors 105 to be detected. The detector 211 could detect changes in the way the sensors 105 interact with an input beam of light. In some examples the detector could be an optical coherence tomography detector which is configured to detect the backscattered and/or reflected light. This could be used to detect changes in the size and/or shape of the sensors 105. For example the optical coherence tomography may be configured to detect a change in size of shape of functionalized particles 203 caused by the presence of a parameter.

In examples where the detector 211 comprises an optical detector this enables the physical properties of the sensors 105 to be monitored using a beam of light, or other type of electromagnetic radiation. This may enable the physical properties of the sensor 105 to be monitored without requiring any electrical connections to the sensors 105 or without requiring any electrodes or other coupling devices being added to the subject's skin.

Therefore the example shown in FIGS. 2A and 2D provide an apparatus 101 comprising artificial skin 103 which enables parameters within the subject's skin to be monitored.

In the example shown in FIGS. 2A to 2D the change of the physical property of the sensors 105 is caused by the sensors 105 binding to a parameter. It is to be appreciated that other processes could cause the change in other examples of the disclosure. For instance, in some examples there could be an oxidation or reduction of chemicals within the functionalized particles 203 which could cause a change in the optical properties, or other physical properties, of the functionalized particles 203.

Also in the examples shown in FIGS. 2A to 2D the plurality of sensors 105 have a homogenous distribution through the artificial skin 103. In other examples the distribution does not need to be homogenous. For instance, if the apparatus 101 has been formed by a process such as three dimensional printing the process may be controlled so that selected types of sensors in a selected density are provided at different locations within the apparatus 101. This could enable different types of sensors 105 in different densities to be provided within the same apparatus 101.

Figure 3:
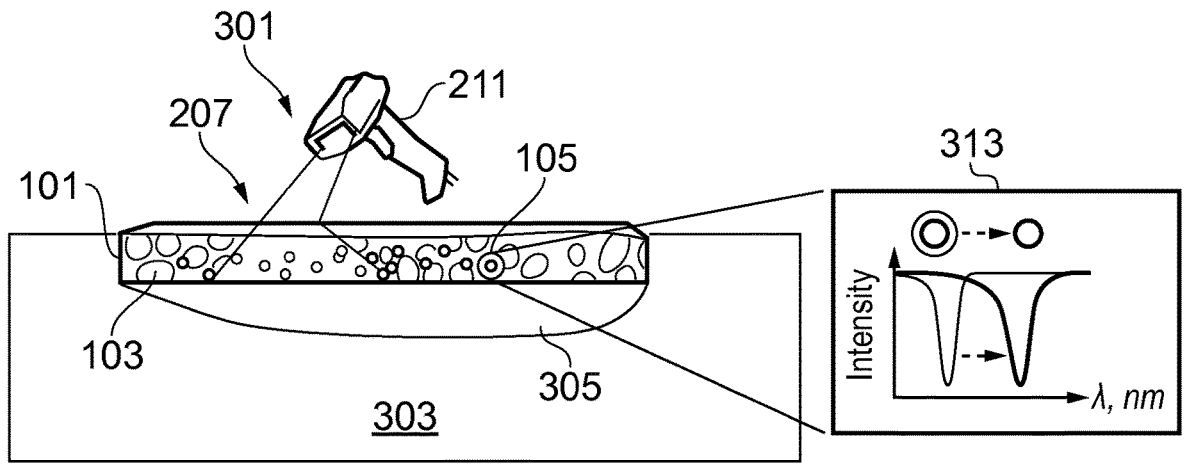
FIG. 3 shows a system comprising an example apparatus.

FIG. 3 shows a system 301 comprising an example apparatus 101 and a detector 211. The example apparatus 101 comprises at least one portion of artificial skin 103, a plurality of sensors 105 dispersed within the artificial skin 103 and a protective layer 207 overlaying the artificial skin 103. The detector 211 could be a handheld optical detector or any other suitable type of detector. The detector 211 is configured to detect modification of the physical properties of the sensors 105.

In the example of FIG. 3 the apparatus 103 is provided covering a wound 305. The apparatus 101 is positioned so that it completely covers the wound 305. In the example of FIG. 3 the apparatus 101 is positioned so that the artificial skin 103 of the apparatus 101 is in contact with the undamaged skin 303 which surrounds the wound 305. This may enable cellular integration of the artificial skin 103 with the undamaged skin 303.

In the example of FIG. 3 the sensors 105 interact with the parameter so as to cause a change in the optical properties of the sensors 105. In the example of FIG. 3 the change could be the change in the wavelength of light that is absorbed by the sensors. This change in the absorption of the light then produces a change in the relative intensity of the light that is detected by the detector 211. Plot 313 shows how the intensity of the light detected by the detector 211 may change as the physical properties of the sensor 105 is modified. The wavelengths of light that are detected can be determined using spectral analysis or any other suitable means. The outputs of the detector 211 can therefore give an indication of the presence of the parameter within the wound 305.

Figures 4A, 4B:
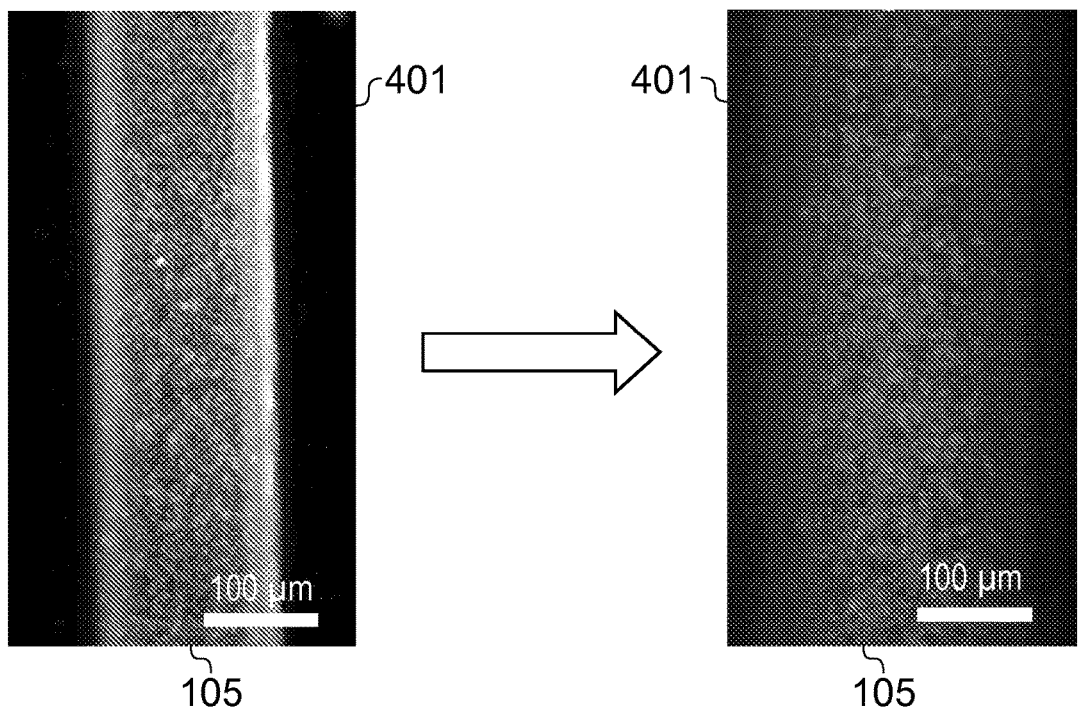
FIGS. 4A and 4B show an example sensor.

FIGS. 4A and 4B show an example sensor 105 which may be used in some examples of the disclosure. FIG. 4A shows the sensor 105 before it has been exposed to a parameter and FIG. 4B shows the sensor 105 after it has been exposed to a parameter.

In the example of FIGS. 4A and 4B the sensor 105 is degraded by exposure to the parameter. The parameter could be a chemical entity that is present in the subject's skin. The parameter could be a chemical entity that is present in a wound. Other parameters could be used in other examples of the disclosure.

In the example of FIGS. 4A and 4B the sensor 105 comprises an elongated microparticle 401. The elongated microparticle 401 has a diameter of the order of 100 micrometers. In some examples the elongated microparticle 401 could provide a microfibre.

Before the elongated microparticle 401 is exposed to the parameter the elongated microparticle 401 has clearly defined edges. The clearly defined edges are shown in FIG. 4A. After the elongated microparticle 401 has been exposed to the parameter the edges have degraded so that they are no longer clearly defined. This degraded elongated microparticle 401 is shown in FIG. 4B. The degradation of the edges of the elongated microparticle 401 changes the shape of the elongated microparticle 401. This change in shape can be detected by a detector 211 such as an optical coherence tomography detector.

The degradation of the edges of the elongated microparticle 401 may also cause changes in other physical properties of the sensor 105 such as the refractive index of the wavelengths of light that are absorbed by the elongated microparticle 401. These changes can be detected by an optical detector or by any other suitable means.

FIGS. 5A and 5B show another example sensor 105 which may be used in some examples of the disclosure. FIG. 5A shows the sensor 105 before it has been exposed to a parameter and FIG. 5B shows the sensor 105 after it has been exposed to a parameter.

In the example of FIGS. 5A and 5B the sensor 105 is degraded by exposure to the parameter. The parameter could be a chemical entity that is present in the subject's skin. The parameter could be a chemical entity that is present in a wound. Other parameters could be used in other examples of the disclosure.

In the example of FIGS. 5A and 5B the sensor 105 comprises a substantially spherical microparticle 501. FIGS. 5A and 5B show a cross section of the substantially spherical microparticle 501. The substantially spherical microparticle 501 has a diameter of the order of 20 micrometers.

Before the substantially spherical microparticle 501 is exposed to the parameter the substantially spherical microparticle 501 has clearly defined edges. The clearly defined edges are shown in FIG. 5A. After the substantially spherical microparticle 501 has been exposed to the parameter the edges have degraded so that they are no longer clearly defined. This degraded substantially spherical microparticle 501 is shown in FIG. 5B. The degradation of the edges of the substantially spherical microparticle 501 changes the shape of the substantially spherical microparticle 501. This change in shape can be detected by a detector 211 such as an optical coherence tomography detector.

The degradation of the edges of the substantially spherical microparticle 501 may also cause changes in other physical properties of the sensor 105 such as the refractive index of the wavelengths of light that are absorbed by the substantially spherical microparticle 501. These changes can be detected by an optical detector or by any other suitable means.

FIGS. 6A and 6B show another example sensor 105 which may be used in some examples of the disclosure. FIG. 6A shows the sensor 105 before it has been exposed to a parameter and FIG. 6B shows the sensor 105 after it has been exposed to a parameter.

In the example of FIGS. 6A and 6B the sensor 105 is modified by exposure to the parameter so that the contrast of the sensor 105 relative to the artificial skin 103 changes. The parameter could be a chemical entity that is present in the subject's skin. The parameter could be a chemical entity that is present in a wound. Other parameters could be used in other examples of the disclosure.

In the example of FIGS. 6A and 6B the sensor 105 comprises a substantially spherical microparticle 601. The substantially spherical microparticle 601 could have a diameter of any suitable size.

Before the substantially spherical microparticle 601 is exposed to the parameter the substantially spherical microparticle 601 has clearly defined edges which show a strong contrast with the surrounding material as shown in FIG. 6A. After the substantially spherical microparticle 601 has been exposed to the parameter the edges have been modified so that they are no longer clearly defined and the contrast with the surrounding material is less strong. This degraded substantially spherical microparticle 601 is shown in FIG. 6B. The change in the contrast between the substantially spherical microparticle 601 and the surrounding material can be detected by a detector 211 such as an optical coherence tomography detector or by ant other suitable means.

Examples of the disclosure provide an apparatus 101 comprising artificial skin 103 which enables internal monitoring of the user's skin. As the sensors 105 for monitoring the biometric markers or other parameter are dispersed within the artificial skin 103 this enables the parameters to be directly monitored without having to disturb the artificial skin 103. This allows for non-invasive monitoring of the wound. For example there is no need to remove the artificial skin 103 in order to monitor a wound underneath apparatus 101.

In some examples the apparatus 101 could be used to monitor other biometric markers of a subject that are not related to wound healing. For example the apparatus 101 could be used to monitor glucose levels or any other suitable parameter. This could allow for long term monitoring of the physical condition of a subject. The long term monitoring aspect could be configured to cover a time period of weeks or months or even longer.

As the sensors 105 are distributed within the artificial skin 103 this provides for a lightweight and compact method of monitoring the parameters of the user. The example apparatus 101 do not require any additional connectors or electrodes to be coupled to a user in order to enable the parameter to be monitored.

The term 'comprise' is used in this document with an inclusive not an exclusive meaning. That is any reference to X comprising Y indicates that X may comprise only one Y or may comprise more than one Y. If it is intended to use 'comprise' with an exclusive meaning then it will be made clear in the context by referring to 'comprising only one . . . ' or by using 'consisting'.

In this description, reference has been made to various examples. The description of features or functions in relation to an example indicates that those features or functions are present in that example. The use of the term 'example' or 'for example' or 'can' or 'may' in the text denotes, whether explicitly stated or not, that such features or functions are present in at least the described example, whether described as an example or not, and that they can be, but are not necessarily, present in some of or all other examples. Thus 'example', 'for example', 'can' or 'may' refers to a particular instance in a class of examples. A property of the instance can be a property of only that instance or a property of the class or a property of a sub-class of the class that includes some but not all of the instances in the class. It is therefore implicitly disclosed that a feature described with reference to one example but not with reference to another example, can where possible be used in that other example as part of a working combination but does not necessarily have to be used in that other example.

Although embodiments have been described in the preceding paragraphs with reference to various examples, it should be appreciated that modifications to the examples given can be made without departing from the scope of the claims.

Features described in the preceding description may be used in combinations other than the combinations explicitly described above.

Explicitly indicate that features from different embodiments (e.g. different methods with different flow charts) can be combined, to Although functions have been described with reference to certain features, those functions may be performable by other features whether described or not.

Although features have been described with reference to certain embodiments, those features may also be present in other embodiments whether described or not.

The term 'a' or 'the' is used in this document with an inclusive not an exclusive meaning. That is any reference to X comprising a/the Y indicates that X may comprise only one Y or may comprise more than one Y unless the context clearly indicates the contrary. If it is intended to use 'a' or 'the' with an exclusive meaning then it will be made clear in the context. In some circumstances the use of 'at least one' or 'one or more' may be used to emphasis an inclusive meaning but the absence of these terms should not be taken to infer and exclusive meaning.

The presence of a feature (or combination of features) in a claim is a reference to that feature) or combination of features) itself and also to features that achieve substantially the same technical effect (equivalent features). The equivalent features include, for example, features that are variants and achieve substantially the same result in substantially the same way. The equivalent features include, for example, features that perform substantially the same function, in substantially the same way to achieve substantially the same result.

In this description, reference has been made to various examples using adjectives or adjectival phrases to describe characteristics of the examples. Such a description of a characteristic in relation to an example indicates that the characteristic is present in some examples exactly as described and is present in other examples substantially as described.

The use of the term 'example' or 'for example' or 'can' or 'may' in the text denotes, whether explicitly stated or not, that such features or functions are present in at least the described example, whether described as an example or not, and that they can be, but are not necessarily, present in some of or all other examples. Thus 'example', 'for example', 'can' or 'may' refers to a particular instance in a class of examples. A property of the instance can be a property of only that instance or a property of the class or a property of a sub-class of the class that includes some but not all of the instances in the class. It is therefore implicitly disclosed that a feature described with reference to one example but not with reference to another example, can where possible be used in that other example as part of a working combination but does not necessarily have to be used in that other example Whilst endeavoring in the foregoing specification to draw attention to those features believed to be of importance it should be understood that the Applicant may seek protection via the claims in respect of any patentable feature or combination of features hereinbefore referred to and/or shown in the drawings whether or not emphasis has been placed thereon.

We claim:

1. An apparatus comprising:
   at least one portion of artificial skin;
   a plurality of light-detectable sensors dispersed within the at least one portion of artificial skin;
   wherein types of light-detectable sensors of the plurality of light-detectable sensors have at least one physical property which is configured to be modified when the types of light-detectable sensors are exposed to a parameter such that the modification of the physical property can be detected by an external detector, wherein the types of light-detectable sensors comprise defined edges having contrast with the artificial skin and the at least one physical property configured to be modified is a degradation of the defined edges; and
   wherein the types of light-detectable sensors are configured to provide an output optical signal that is dependent upon the degradation of the defined edges.

2. An apparatus as claimed in claim 1 comprising a protective surface provided overlaying the at least one portion of artificial skin.

3. An apparatus as claimed in claim 2 wherein the protective surface provides an interface between the plurality of light-detectable sensors and the external detector.

4. An apparatus as claimed in claim 1 wherein the at least one portion of artificial skin is configured to integrate with the skin of a subject.

5. An apparatus as claimed in claim 1 wherein the at least one portion of artificial skin is configured to cover a wound of a subject.

6. An apparatus as claimed in claim 1 wherein the at least one portion of artificial skin is configured to conform to the shape of a subject's damaged skin.

7. An apparatus as claimed in claim 1 wherein the at least one portion of artificial skin comprises a matrix of skin tissue which is configured to support the plurality of light-detectable sensors.

8. An apparatus as claimed in claim 1 wherein the types of light-detectable sensors comprise functionalized particles.

9. An apparatus as claimed in claim 8 wherein at least one of the functionalized particles is configured to bind to a chemical entity so that the binding modifies a physical property of the functionalized particle.

10. An apparatus as claimed in claim 8 wherein the functionalized particles have a diameter which is less than 100 micrometers.

11. An apparatus as claimed in claim 1 wherein the apparatus further comprises a plurality of different types of sensors where the different types of sensors are configured to detect different parameters and/or the different types of sensors have different shapes.

12. An apparatus as claimed in claim 1 wherein the parameter that is detected by the plurality of sensors comprises at least one of: glucose levels, bacteria, temperature, pH level, chemical entity, moisture, or oxygenation levels.

13. An apparatus as claimed in claim 1 wherein the physical property of the types of light-detectable sensors that is modified comprises a size of the sensor.

14. An apparatus as claimed in claim 1 wherein the external detector comprises an optical coherence tomography detector.

* * * * *